(12) United States Patent
Prohaska et al.

(10) Patent No.: US 7,404,882 B2
(45) Date of Patent: *Jul. 29, 2008

(54) FILM-TYPE SOLID POLYMER IONOMER SENSOR AND SENSOR CELL

(75) Inventors: Otto J. Prohaska, Danbury, CT (US); Anthony B. LaConti, Lynnfield, MA (US); Jose D. Giner, Brookline, MA (US); Mourad Manoukian, Watertown, MA (US)

(73) Assignee: PerkinElmer LAS, Inc., Boston, MA (US)

( * ) Notice: Subject to any disclaimer, the term of this patent is extended or adjusted under 35 U.S.C. 154(b) by 903 days.

This patent is subject to a terminal disclaimer.

(21) Appl. No.: 10/738,858

(22) Filed: Dec. 17, 2003

(65) Prior Publication Data

US 2004/0129565 A1    Jul. 8, 2004

Related U.S. Application Data

(63) Continuation of application No. 09/443,875, filed on Nov. 19, 1999, now Pat. No. 6,682,638.

(51) Int. Cl.
*G01N 27/407* (2006.01)
(52) U.S. Cl. .................. 204/426; 204/424; 204/431
(58) Field of Classification Search .............. 204/424, 204/426, 431, 432
See application file for complete search history.

(56) References Cited

U.S. PATENT DOCUMENTS 3,934,193 A    1/1976   Hall
3,972,682 A    8/1976   Stephens et al.

(Continued)

FOREIGN PATENT DOCUMENTS

DE    199 40 095 A1    1/2001

(Continued)

OTHER PUBLICATIONS

Toxic Gas Citicels, product manual from City Technology, pp. 2-39, published on or before Jul. 30, 1999.*

(Continued)

*Primary Examiner*—Kaj K Olsen
(74) *Attorney, Agent, or Firm*—St. Onge Steward Johnston & Reens LLC

(57) ABSTRACT

A miniaturized gas sensor including film type electrodes, and a solid ionomer electrolyte, for the detection of toxic gases, i.e., carbon monoxide, and other oxidizable or reducible gases and vapors is described. The all-solid planar sensor cell has two or more film type electrodes arranged on a non-conductive planar surface of a supportive material. The electrodes are discrete and in intimate contact with the same solid polymer ionomer membrane. The sensor cell contains no liquid electrolyte and is operated in a potentiostatic or potentiodynamic mode. The unique feature of the sensor cell is that high sensitivity to a select gas or vapor is achieved by a novel three-phase contact area design for a sensing electrode which is easily accessible to the gas sample via small diffusion openings or holes that penetrate through the solid polymer ionomer membrane layer above the sensing electrode. A significant signal to background noise enhancement is achieved for these film type sensor cells by processes that increase the three-phase contact area.

17 Claims, 7 Drawing Sheets

U.S. PATENT DOCUMENTS

| | | | |
|---|---|---|---|
| 4,032,296 | A | 6/1977 | Hall |
| 4,038,053 | A | 7/1977 | Golay |
| 4,172,770 | A | 10/1979 | Semersky et al. |
| 4,440,726 | A | 4/1984 | Coulson |
| 4,555,383 | A | 11/1985 | Hall |
| 4,032,296 | A | 1/1987 | Hall |
| 4,649,124 | A | 3/1987 | Hall |
| 4,812,221 | A | 3/1989 | Madou et al. |
| 4,820,386 | A | 4/1989 | LaConti et al. |
| 4,851,104 | A | 7/1989 | Connery et al. |
| 4,900,405 | A | 2/1990 | Otagawa et al. |
| 5,194,814 | A | 3/1993 | D'Couto |
| 5,302,274 | A | 4/1994 | Tomantschger et al. |
| 5,322,602 | A | 6/1994 | Razaq |
| 5,331,310 | A | 7/1994 | Stetter et al. |
| 5,525,197 | A | 6/1996 | Coulson |
| 5,527,446 | A | 6/1996 | Kosek et al. |
| 5,545,252 | A | 8/1996 | Hinshaw et al. |
| 5,573,648 | A | 11/1996 | Shen et al. |
| 5,650,054 | A | 7/1997 | Shen et al. |
| 5,711,786 | A | 1/1998 | Hinshaw |
| 5,830,337 | A | 11/1998 | Xu |
| 5,889,197 | A | 3/1999 | van der Maas et al. |
| 5,985,673 | A | 11/1999 | Bao et al. |
| 6,080,294 | A | 6/2000 | Shen et al. |
| 6,165,251 | A | 12/2000 | Lemieux et al. |
| 6,200,443 | B1 | 3/2001 | Shen et al. |
| 6,205,841 | B1 | 3/2001 | Shibamoto |
| 6,245,298 | B1 | 6/2001 | Bremer et al. |
| 6,287,643 | B1 | 9/2001 | Powell et al. |
| 6,306,489 | B1 | 10/2001 | Hellmann et al. |
| 6,309,612 | B1 | 10/2001 | Balachandran et al. |
| 6,338,823 | B1 | 1/2002 | Furukawa |
| 6,355,150 | B1 | 3/2002 | Savin-Poncet et al. |

FOREIGN PATENT DOCUMENTS

| | | |
|---|---|---|
| DE | 199 44 650 A1 | 12/2001 |
| EP | 0 157160 A1 | 9/1985 |
| GB | 1382640 | 6/1972 |
| GB | 1382649 | 8/1972 |
| WO | WO 95/14226 | 5/1995 |

OTHER PUBLICATIONS

Kimura et al, Principles and Development of a Thick-Film Zirconium Oxide Oxygen Sensor, pp. 101-120 from ACS Symposium Series 309, Fundamentals and Applications of Chemical Sensors, 1986.*
Supplementary European Search Report, Oct. 31, 2006, 3 pages.
(Polyaniline thin-films for gas sensing), N.E. Agbor et al., 1995 Elsevier Science S.A. pp. 173-179.
(The Development of a Thick-Film Electrochemical Sensor and Instrumentation for In-Situ Determination of Carbon Dioxide Partial Pressure ($pCO_2$) In The Marine Environment), M.R. Creasey et al., University of Southampton, U.K., Electronic Engineering in Oceanography, Jul. 19-21, 1994, Conference Publication No. 394 IEE 1994.
(Sixth International Conference on Electronic Engineering in Oceanography) Electron theory of thin-film gas sensors, Helmut Geistlinger, 1993 Elsevier Sequoia, pp. 47-60.
(A Practical Reference Electrode) J. Giner, Pratt & Whitney Aircraft, Division of United Aircraft Corporation, East Hartford, CT.
(Design and application of thick-film multisensors) N. Hampp et al., 1992 Elsevier Sequoia pp. 144-148.
(Thin Film Porous Membranes for Catalytic Sensors) R.C. Hughes, et al., 1997 International Conference on Solid-State Sensors and Actuators Chicago, Jun. 16-19, 1997.
(Amperometric Gas Sensor of Thin Gold Film Electrode Ion-Plated on Gas Permeable Membrane for Detection of Arsine and Silane) Toru Ishiji et al., pp. 1019-1020.
(A solid-state pH sensor based on a Nafion-coated iridium oxide indicator electrode and a polymer-based silver chloride reference electrode) Patrick J. Kinlen et al., 1994 Elsevier Science pp. 13-25.
(Multifunctional Sensors Based on Ceramic Electrolytes) Meilin Liu et al., Georgia Institute of Technology, Atlanta, Georgia pp. 421-427.
(The thick-film route to selective gas sensors) F. Menil et al., 1995 Elsevier Science S.A. pp. 415-420.
(Properties of vanadium oxide thin films for ethanol sensor) G. Micocci et al., J. Vac. Sci. Technol. A 15(1), Jan./Feb. 1997 American Vacuum Society.
(An Integrated Multi-Element Ultra-Thin-Film Gas Analyzer) N. Najuh et al., Solid-State Sensor and Actuator Workshop Proc. 5.
(Preparation of thin gold-film electrode for an electrochemical gas sensor for phosphine and arsine) Nobuo Nakano, et al., 1994 Elsevier Science S.A. pp. 51-55.
(A Study of the Surface Sensitivity of Tin Oxide Sensors To Carbon Monoxide and Dioxide) Dario Narducci et al., Dept. of Physical Chemistry & Electrochemistry v. C. Golgi, 19 I-20133 Milano (Italy).
(UV-Polymerizable Screen-Printed Enzyme Pastes) Ingrid Rohm, et al., 1995 American Chemical Society Analytical Chemistry, vol. 67, No. 13, Jul. 1, 1995, Anal. Chem. 1995, 67,2304-3207.
(CO-Sensor for domestic use based on high temperature stable $Ga_2O_3$ thin films), T. Schwebel, et al., 1997 International Conference on Solid-State Sensors and Actuators Chicago, Jun. 16-19, 1997.
(A Low-Power CMOS Compatible Integrated Gas Sensor Using Maskless Tin Oxide Sputtering) Lie-yi Sheng, et al., 1997 International Conference on Solid-State Sensors and Actuators Chicago, Jun. 16-19, 1997 pp. 939-942.
(Platinum Thin Films and Next-Generation Micromachined Sensors) John Staley, et al., Sensors Apr. 1996.
(An amperometric carbon monoxide sensor based on the steady-state difference response technique) Y. Tan et al., 1995 Elsevier Science S.A. pp. 113-121.
(A Novel Semiconductor No Gas Sensor Operating At Room Temperature) Zhang Wenyi et al., 1997 International Conference on Solid-State Sensors and Actuators, Chicago, Jun. 16-19, 1997.
(Environmental gas sensing) Noboru Yamazoe et al., 1994 Elsevier Science S.A. pp. 95-102.
(Life-elongation mechanism of the polymer-electrolyte lamination on a CO sensor) Ayumu Yasuda, et al., 1994 Elsevier Science S.A. pp. 229-236.
Analytik Jena AG acquires 100% of APS Technologies, Inc./USA Jena/Houston, Sep. 24, 2001, 2 pgs.
Total Sulfur Analyzer—Combustion / Electrochemical Detection*; APS Technologies, Inc.; ASTM D6428-99; 40 CFR 80.580; 2 pgs.
Versatile Electrolytic Conductivity Detector For Gas Chromatography, P. Jones and G. Nickless, J. Chromatogr., 73 (1972), 19-28.
Electrolytic Conductivity Detector for Gas Chromatography, Dale M. Coulson, Coulson Instruments Co., J. Gas Chromatography, Apr. 1965.
Carbon Monoxide Sensors, Beech et al., Electrochemistry at Loughborough, 1999.

* cited by examiner

FILM-TYPE SOLID POLYMER IONOMER SENSOR AND SENSOR CELL

PRIORITY APPLICATION

This application is a continuation of U.S. patent application Ser. No. 09/443,875 for a "Film Type Solid Polymer Ionomer Sensor and Sensor Cell" filed Nov. 19, 1999, now U.S. Pat. No. 6,682,638.

FIELD OF THE INVENTION

The invention is in general directed toward a gas sensor and in particular to a miniaturized gas sensor with film type electrodes and a solid ionomaer electrolyte.

BACKGROUND OF THE INVENTION

Film based techniques have been investigated for a wide variety of sensors, as reported by Wenyi et al., 1997; Hughes et al., 1997; Staley, 1996; Agbor et al., 1995; Tan and Tan, 1995; Menil et al., 1994; Kunnecke et al., 1994; Creasey and Varney, 1994; Geistlinger, 1993; Ishiji et al., 1993; Najafi et al., 1992; Hampp et al., 1992; Nakano and Ogawa, 1994; and Yamazoe and Miura, 1994. While solid-state gas sensors have the advantage of being able to operate at elevated temperatures, they also have the disadvantages of slow response and recovery time and a high internal operating temperature as reported by Liu et al., 1993; Narducci et al., 1993 and more recently by Schwebel et al., 1997; Sheng et al., 1997; and Micocci et al., 1997. Substantial development work needs to be done with this type of sensors before they can be utilized in battery-powered sensor instruments.

A Nafion®-coated metal oxide pH sensor was reported (Kinlen et al., 1994) with sputtered iridium oxide sensing and silver/silver chloride reference electrodes on alumina ceramic substrates. Nafion was used as a cation-selective ionomer coating in order to decrease the oxidation-reduction error generally affecting the performance of metal oxide pH electrodes. The use of Nafion as a polymer-electrolyte for a thin-film CO sensor was described (Yasuda et al., 1994) with macro-sized, sputtered Pt sensing electrodes and counter electrodes and a smaller, sputtered Au electrode as a reference electrode. A 5 wt % n-propyl alcohol solution of Nafion (DuPont, 1100 EW) was used to form the polymer electrolyte film over the electrodes by casting. The polymer was washed and protonated in aqueous sulfuric acid prior to casting. The lifetime of this sensor was reported to be less than one month. During this one month lifetime the CO oxidation current decreased steadily down to a few percent of its original value without any period of stable measurement signal. The lifetime of the device may be extended by up to three years by lamination of the polymer electrolyte layer with a cast perfluorocycloether-polymer film in order to keep the CO permeability coefficient through Nafion constant. Theoretical calculations showed that the drift rate of the signal could be significantly reduced under these conditions.

Descriptions of typical state-of-the-art hydrated solid polymer electrolyte or ionomer sensors and sensor cells are provided by Kosek et al. U.S. Pat. No. 5,527,446; LaConti and Griffith, U.S. Pat. No. 4,820,386; Shen et al., U.S. Pat. No. 5,573,648; and, Stetter and Pan, U.S. Pat. No. 5,331,310. These sensor cells, based on hydrated solid polymer electrolyte or ionomer technology, have several advantages over conventional electrochemical sensor cells. The catalytic electrodes are bonded directly to both sides of a proton conducting solid polymer ionomer membrane providing a stable electrode to electrolyte interface. One side of the electrolyte membrane is flooded with distilled water, making the sensor cell self-humidifying and independent of external humidity. Since no corrosive acids or bases are used in the sensor cell, over 10 years lifetime has been demonstrated for solid polymer ionomer sensor cells. Finally, the sensor cells are easy to maintain, thus ideal for use in remote, unattended environments. Regular addition of water to the reservoir in the sensor housing every several months, and monthly calibration checks are the only requirements.

A disadvantage of the state-of-the-art sensors described above is that the signal-to-noise ratio may not be conducive to the detection of very low concentrations (parts per billion, ppb) of important environmental and biomedical gases and vapors. Also, response time may be relatively slow, and reproducibility between sensors and sensor cells may be difficult to achieve. The sensors are also relatively costly.

SUMMARY OF THE INVENTION

The objective of this invention is to overcome the present limitations of miniaturized electrochemical sensors by uniquely interfacing advanced solid polymer ionomer membrane configurations with film type electrode structures to obtain low maintenance, highly sensitive, rapidly responsive, reproducible, sensor devices for environmental, industrial, and biomedical monitoring. By using a uniquely designed film type electrode array in intimate contact with an advanced solid polymer ionomer membrane film configuration, to form a three-phase contact area for the sensing electrode, where the gas sample, the electrode, and the solid ionomer can interface, a superior signal-to-noise ratio, rapid response time, and reproducibly of at least 1 to 10 ppb for a selected gas in an ambient environment can be achieved. Also, the projected cost of these sensors and sensor cells is very low since established film type solid-state manufacturing processes can be utilized.

The invention is also directed toward a treatment process for catalytically activating an ionomer membrane.

The invention is still further directed toward a gas sensor utilized in conjunction with a gas sensor control circuit.

The invention is also directed toward a gas sensor utilized in a gas sensing instrument.

DETAILED DESCRIPTION OF THE INVENTION

Figure 1:
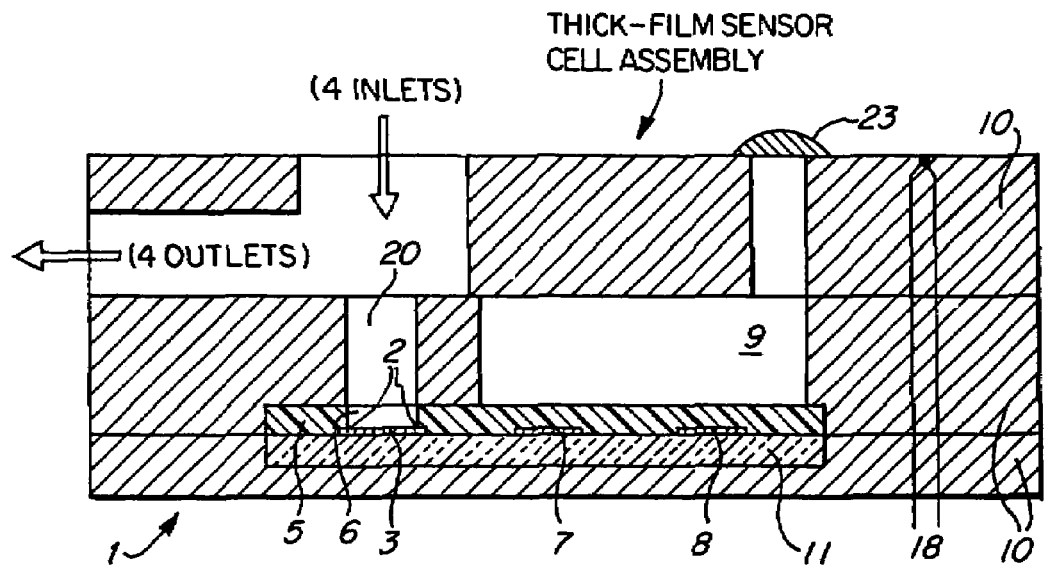
FIG. 1 shows a cross-sectional view of the film type planar sensor cell.

In FIG. 1, the film type sensor cell assembly (1) includes a three-phase contact area (2) for the sensing electrode (3), where the gas sample (4), the sensing electrode (3), and the solid ionomer membrane (5) can interface, as an essential part of the sensor design. The three-phase contact area (2) is formed by openings (6), i.e., of circular shape, about 1.0 mm in diameter, in the solid ionomer membrane (5) over the sensing electrode (3). The sensor exhibits a fast response time because the solid ionomer membrane (5) layer acts simply as a proton conducting element between the film type sensing (3), reference (7), and counter (8) electrodes. Signal response is further enhanced by a special ionomer membrane treatment process which serves to "catalytically activate" the membrane. During this process platinum is imbedded in the solid ionomer membrane (5). The improved response is due to the fact that the Pt, incorporated into the membrane (5), contributes to the signal generation in the three-phase contact area (2). The finely dispersed platinum is immobilized within and on the surface of the membrane (5) and does not affect the membrane's (5) ionic conductivity or water content. Also, this finely dispersed catalyst within the membrane (5) catalytically reacts with the permeating gases and prevents any reactive gases from reaching the reference electrode (7), and disturbing it from its Pt/air ($O_2$) rest potential.

The film type sensor cell assembly shown in the schematic drawing of FIG. 1 includes a water reservoir (9) to keep the solid ionomer membrane (5) hydrated. The water reservoir (9) is sealed with a cap (23). When using the devices in a humid atmosphere, a water reservoir (9) may not be required and would make the sensor housing design (10) significantly simpler, while the device could be packaged under humidified condition, ready for use.

Alternatively the openings in the ionomer membrane (6) can be slits or other suitable configurations for interfacing to form a three-phase contact area (2). Also, in order to enhance the magnitude of the signal response and long-term stability, alternative materials such as Pt, gold, $RuO_2$ or other select metal or metal oxides can be deposited within the ionomer membrane (5) as finely dispersed particles.

Figure 2A:
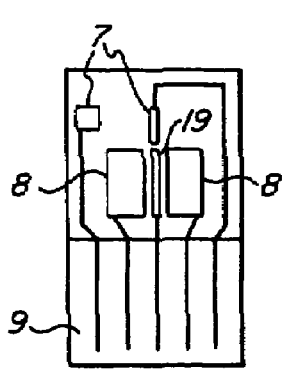
FIG. 2a, shows a band-type film type sensing electrode.
Figure 2B:
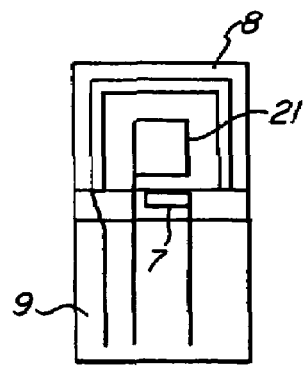
FIG. 2b, shows a flag-type film type sensing electrode.

Some select film type electrode configurations on non-conductive planar surfaces of a supporting material (11), i.e., of alumina substrates, are showing practical sensing (3), counter (8) and reference (7) electrode design in FIG. 2.

Figure 3:
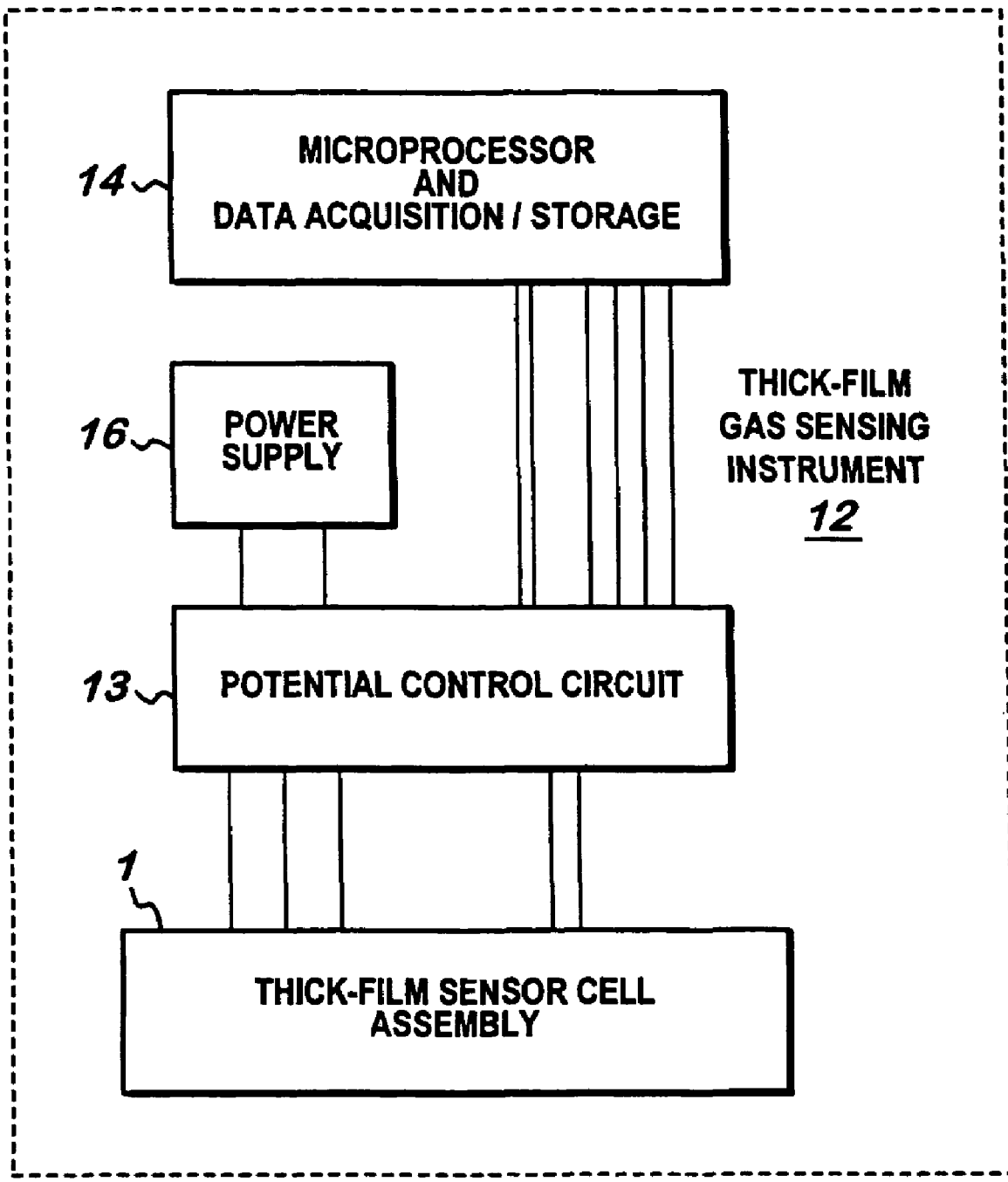
FIG. 3 shows a block diagram of the complete film type gas or vapor sensing instrument.
Figure 4:
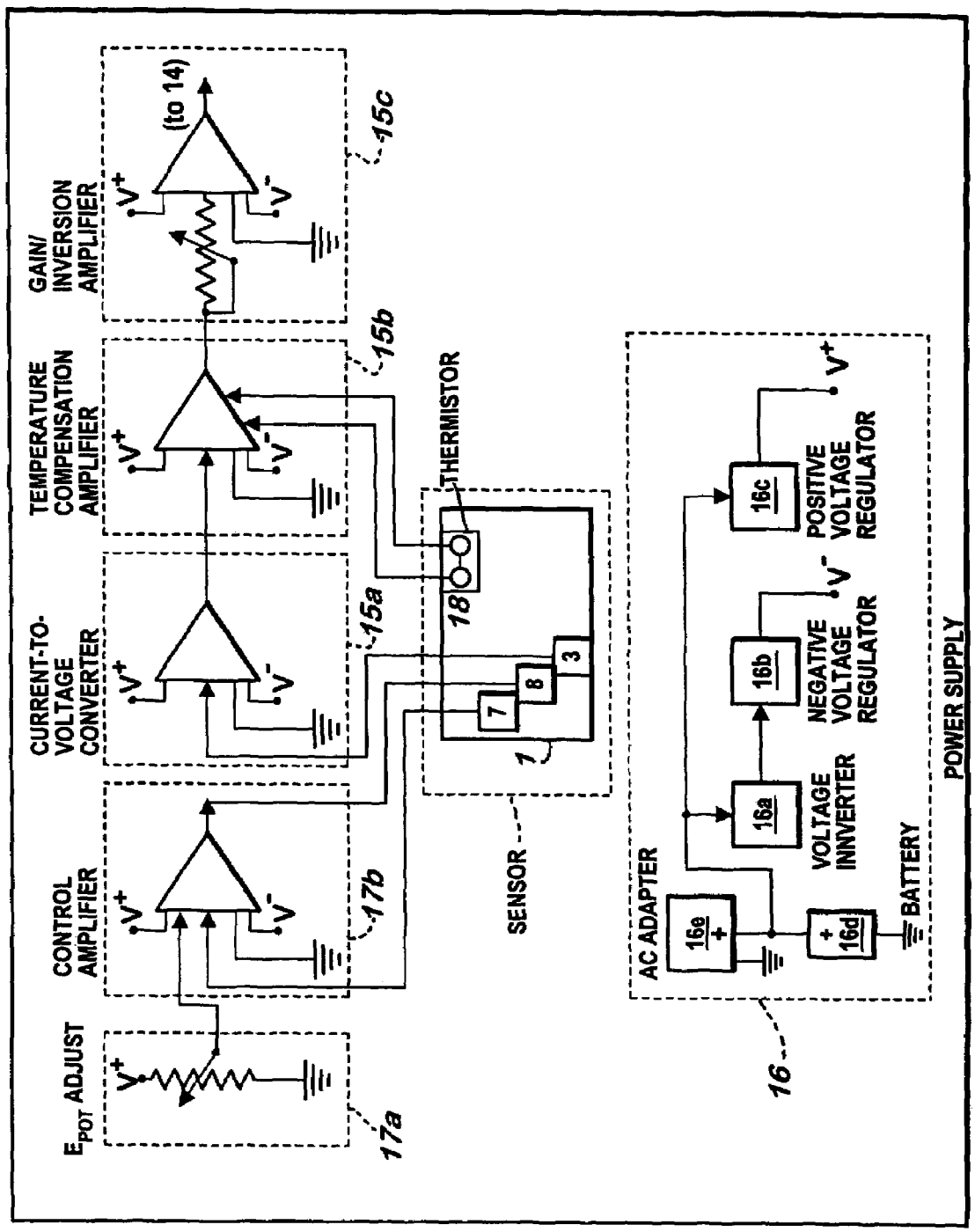
FIG. 4 shows a schematic of the gas sensor control circuits.
Figure 5:
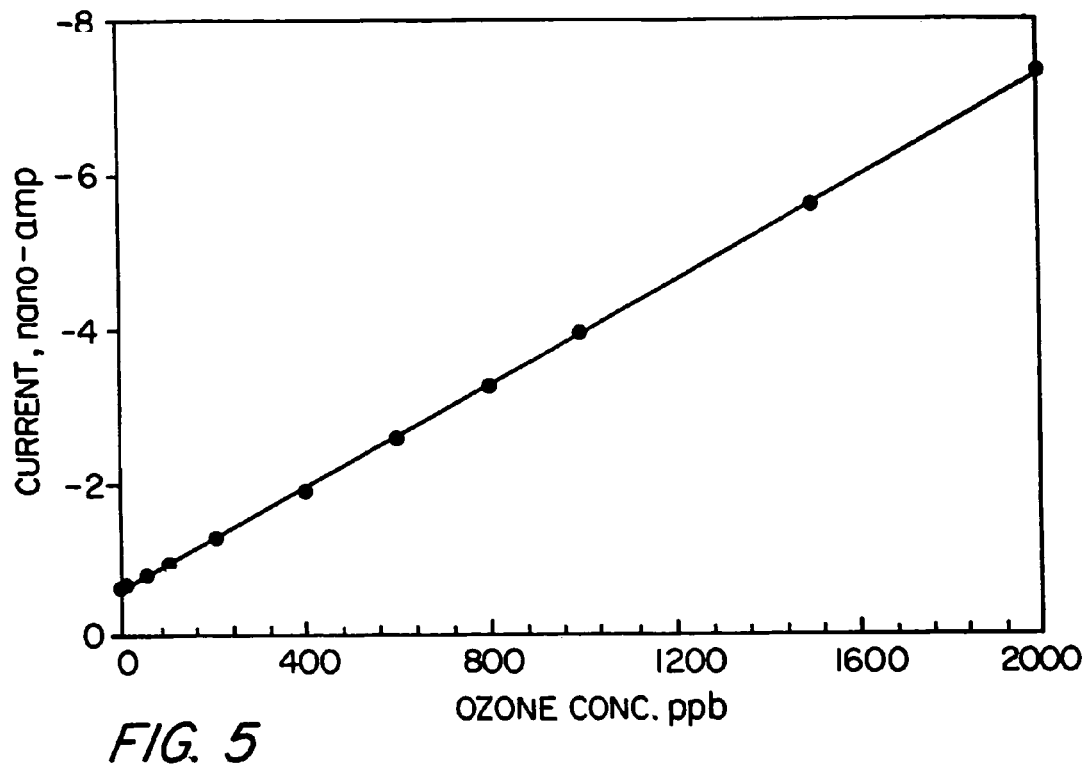
FIG. 5 shows a calibration curve for ozone in air with band-type Au sensing electrode.
Figure 6:
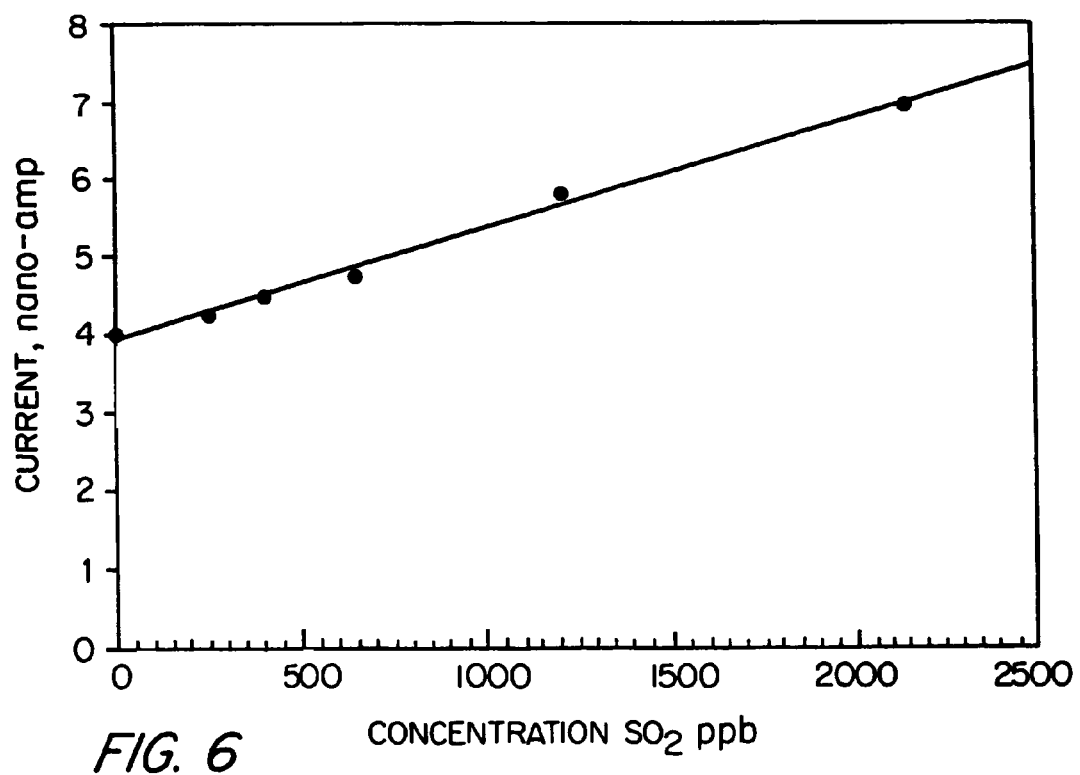
FIG. 6 shows a calibration curve for $SO_2$ in air with band-type Pt sensing electrode.
Figure 7:
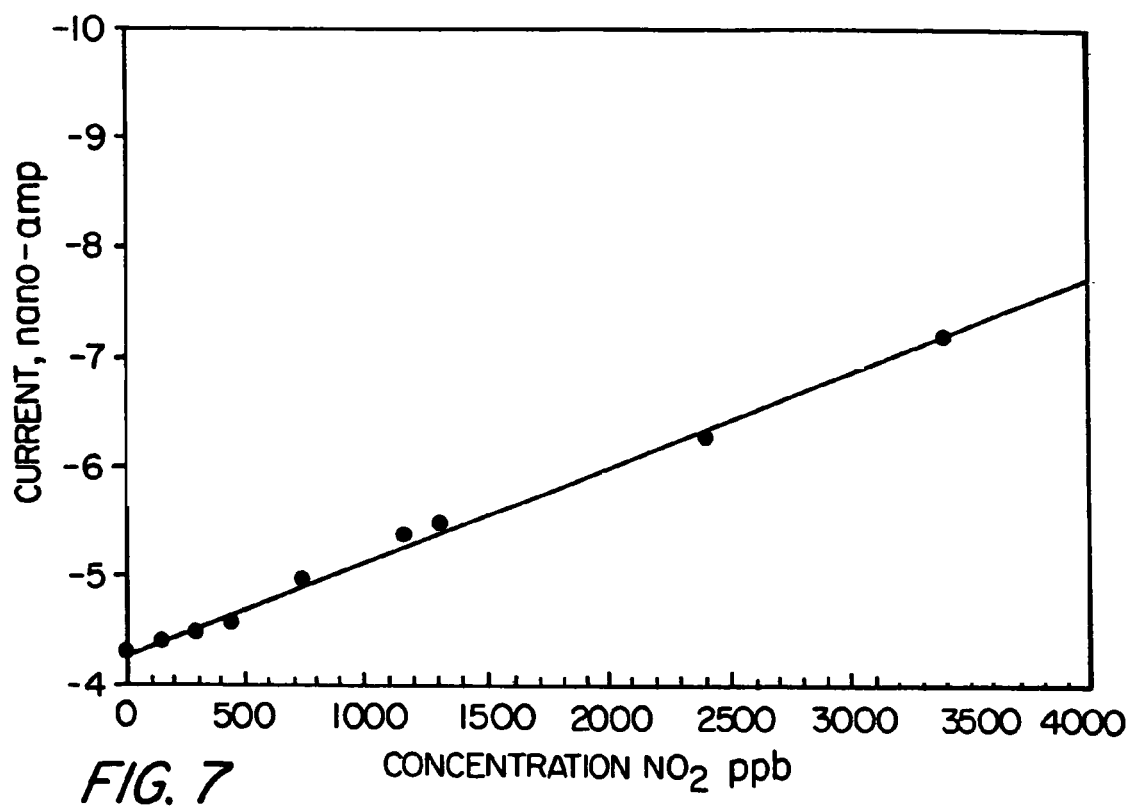
FIG. 7 shows a calibration curve for $NO_2$ in air with band-type Au sensing electrode.
Figure 8:
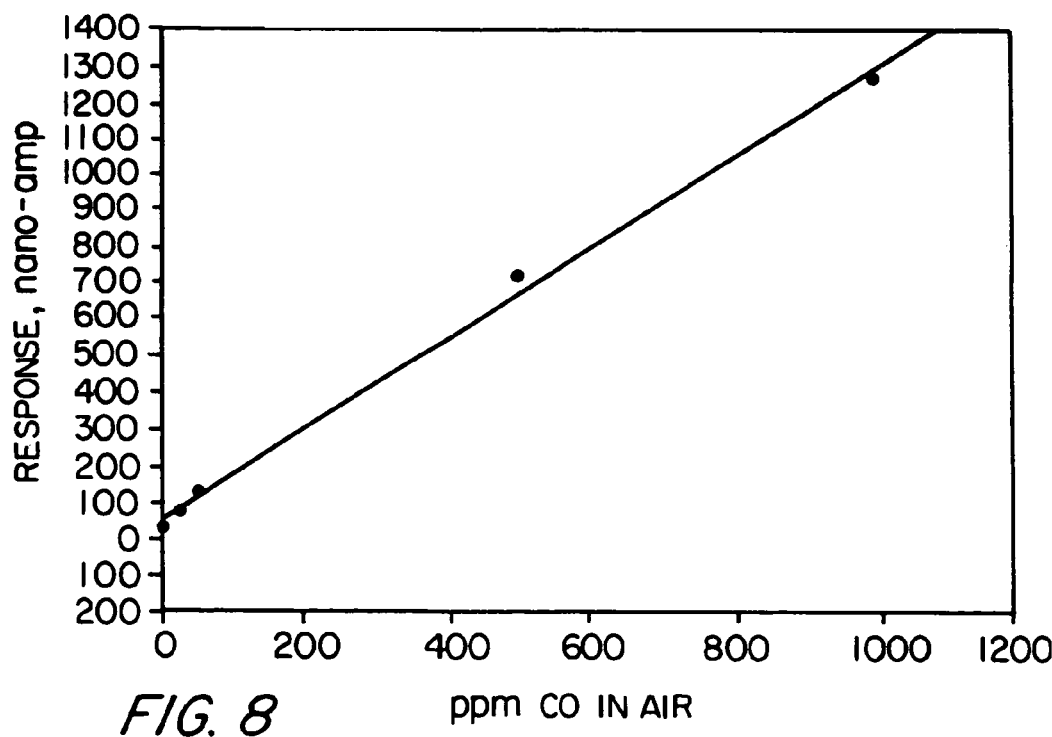
FIG. 8 shows a calibration curve for CO in air with band-type Pt sensing electrode.

A block diagram of the complete film type gas or vapor sensing instrument (12) is shown in FIG. 3. A schematic of the gas sensor control circuits is shown in FIG. 4. The sensor assembly (1) and its potential-control circuit (13) are integrated with a battery-operated microprocessor (14) of 32K memory, which samples the sensor signal as well as temperature and other signals at 10-, 20-, or 30-second intervals and stores an average value at intervals of 2, 5, or 10 minutes according to a programmable protocol. The data acquisition/ storage unit in the microprocessor (14) can record 8 days of data, storing at 2-minute intervals, or up to 40 days storing at 10-minute intervals. In clinical testing to date, a 2-minute interval is suitable for one-day clinical studies and a 10-minute interval is appropriate for extended use. The microprocessor (14) with data acquisition/logic circuit can be programmed to sample more than one analog signal from the control circuit (13), and to convert these to digital signals and store them (i.e., gas concentration and temperature) at preset intervals together with real-time data. Data are off-loaded to a personal computer by accessing the microprocessor (14) through an RS232 port. After downloading, the digital data are converted to engineering units of gas concentration and temperature, and can be graphed by a menu-driven Lotus® 123 spreadsheet. Through a potentiometer in the gain amplifier circuit (15c), the device can be calibrated with calibrated gas samples, to indicate gas concentrations in the ambient. The potential-control circuit (13) shown in FIG. 3 is powered, in a preferred embodiment, by six, 1½ volt AA-size batteries (16d). A typical microprocessor (14) with data acquisition-recording capability that has been successfully used is sold by ONSET Computers, Falmouth, Mass., under the product name of "Tattletale Lite®." The sensor assembly (1) with its control circuit (13) is also designed to yield a current or voltage signal proportional to gas flux that could be used to continuously transmit the data to a remote receiving device or central monitoring station or unit.

The film type gas or vapor sensing instrument (12), which is shown in FIG. 3, includes the film type sensor cell assembly (1), potential-control circuitry (13), and the microprocessor (14) with the data acquisition-recording unit. The sensing instrument (12) is preferably battery operated, and has the ability to sample the gas or vapor and temperature signals at intervals and store in the random access memory (RAM) on the data acquisition board days to weeks of data. The data acquisition circuit microprocessor is programmed to sample and store the gas concentration signals at preset intervals. Data are off-loaded to a personal computer by accessing the microprocessor through an RS232 port.

The novelty of the measurement process is that it features potential (voltage) control as well as diffusion control through openings (6) in the membrane (5) of the sensor cell (1) for the sensitive and reproducible measurement of gas or vapor. The potential-control circuit (13) (potentiostat) maintains the sensing electrode (3) at a fixed potential above the reference electrode (7) by passing current between the sensing (3) and counter electrode (8). All three electrodes are located on the same surface of solid polymer ionomer (5). A typical potentiostatic circuit for maintaining the sensing electrode (3) at a fixed potential versus a Pt/air (O2) reference (7) is shown in FIG. 4. The preferred potential range for the sensing electrode (3), when detecting easily oxidizable gases such as CO, is 0 to 50 mV above the Pt/air (O2) reference potential, 1.06 to 1.11 V above a Normal Hydrogen Electrode (N.H.E.). The useful potential-control range to avoid or minimize interference from air (O2) is −300 to +300 mV versus the Pt/air (O2) reference. In this potential range, the sensing electrode (3) has a highly active surface and gases or vapors are electrochemically oxidized or reduced very rapidly and completely; there is essentially zero concentration of gas or vapor at the sensing electrode (3) surface. The combined process of potential and diffusion control through openings in the membrane (6) creates a concentration gradient from the bulk gas sample to the sensing electrode (3) surface and results in a steady-state flux of gas or vapor and rapid electrochemical oxidation or reduction.

Referring to FIG. 4, a block diagram of the sensor control circuit (13) is shown. The sensor control circuit (13) is designed to: 1) control the potential of the sensing electrode (3) at a predetermined voltage (the "potentiostatic voltage", or "Epot"); 2) measure the temperature; 3) convert the gas concentration-related current to a temperature-compensated voltage signal; and 4) provide properly amplified voltage to the data acquisition/storage microprocessor (14). An on-board micro power-regulated power supply (16) uses the microprocessor's (14) power supply to provide the required ±3.9 volts for the sensor circuitry. The DC power can be supplied by a 6-V battery (16d) or an AC adaptor (16e).

The control amplifier portion (17b) of the sensor control circuit (13) consists of a micro power operational amplifier (e.g., MAX407 or LM6062). The sensing (3), counter (8) and reference (7) electrode portions of the sensor assembly (1) are in the feedback loop of the control amplifier (17b) as shown in FIG. 4, a standard configuration for potentiostat circuits. An adjustable voltage divider (17a) allows the polarizing voltage (Epot) to be set at a predetermined voltage range such as 0 to 50 mV. This signal is compared to the reference electrode (7) voltage (which appears with it at the summing junction) by the control amplifier (17b) of the sensor control circuit (13). The latter adjusts the current through the sensor cell (1) to minimize the difference between the Epot and the reference electrode (7) voltages.

The resulting sensor cell (1) current (flow of electrons from (3) to (8)), which is linearly related to the concentration of gas, is transformed into a voltage signal by the current-to-voltage converter (15a). Temperature compensation of the sensor signal is effected in the next stage of amplification (15b) using a thermistor (18a) which is positioned in the gas sensor plastic housing (10). The last stage of amplification (15c) provides the necessary inversion of the voltage signal as well as gain adjustment, to permit calibration for normal variations in sensitivity among sensors. The same type of micro power operational amplifier is used for these stages (15a), (15b), (15c) as for the control amplifier (15b). The transformed current signal is directed to an A/D channel on the data acquisition board of the microprocessor (14).

Power for the sensor control circuit (13) is provided by a Duracell 6-V battery (16d) (PX 28A or 28L) through a micro power-regulated power supply (16). The power supply (16) utilizes a voltage inverter (e.g., ICL 7660) (16a) to convert the positive battery voltage to a negative voltage of the same magnitude, and a positive voltage regulator (e.g., MAX663) (16c) and negative voltage regulator (e.g., MAX 664) (16b) to provide a stable ±3.9 volts.

Other embodiments may include protonic as well as anionic-hydroxide ion-exchange solid ionomer membrane—film type configurations, containing the three-phase contact area (2), and can be used to detect important environmental and biomedical gases and vapors including CO, ozone, NO, $NO_2$, $H_2S$, $SO_2$, $CO_2$, hydrogen, hydrazine, ammonia, ethanol, and acetone. Other easily oxidizable or reducible gases such as $Cl_2$, HCl, formaldehyde, ethylene, or acetylene are readily detected at very low levels.

FIG. 2-a, shows an embodiment comprising a band-type film type sensing electrode (19), 0.5×4 mm2 in size, between two 2×4 mm2 rectangular counter electrode (8) structures. Two additional electrodes are included in the design, serving as reference electrodes (7). The electrode closest to the sensing electrode (19) is used as Pt/air reference electrode (7). The film type counter (8) and reference (7) electrodes are electroplated with Pt black to increase their actual surface area. When a Pt sensing electrode (19) is desired, it is also electroplated with Pt black to increase the measured current signal. A Nafion membrane, approximately 4.5 mil thick, is mechanically pressed onto the electrodes through a specially designed sensor housing (10). A single opening (6) in the ionomer membrane (5), approximately 1.0 mm in diameter provides gas access to the novel three-phase contact area (2), where oxidation/reduction of the analyte occurs. The analyte stream is directed over the sensing electrode (2) at moderately low flow rates. The analyte diffuses on to the sensing electrode (2) through a diffusion hole (20) in the sensor housing (10) and membrane (5) which has length-to-diameter ratios of approximately 3 or greater.

According to the present invention, band-type film type sensing electrodes (19) are used to measure most environmental gases, including ozone, SO2, NO2, and CO. Gold sensing electrodes are used when measuring ozone and NO2 and Pt sensing electrodes are used when measuring SO2 and CO. Calibration curves obtained with this design for ozone, SO2, NO2, and CO are shown in FIGS. 5-8.

FIG. 2-b, shows an embodiment comprising a flag-type film type sensing electrode (21), 6×6 mm2, surrounded by a U-shaped counter electrode (8); with a rectangular 1×4.5 mm2 reference electrode (7) located below the sensing electrode (21). Flag-type film type sensing electrodes (21) are used to measure ozone, NO and CO. Gold sensing electrodes are used to measure ozone and NO, while Pt electrode is used to measure CO. The film type counter (8) and reference (7) electrodes are electroplated with Pt black, as well as the sensing electrode (21), when a Pt sensing electrode is desired. As in the embodiment in FIG. 2-a, the solid ionomer electrolyte (5) is mechanically pressed onto the film type electrodes through a specially designed housing (10). Six openings in the membrane (6), approximately 1.0 mm dia. each, expose the three-phase contact areas (2) to the gas sample (4) under investigation. The film type sensor assembled in the specially designed housing (10) is placed in a 40-ml-volume diffusion chamber, to which the analyte is introduced, to simulate oxidation/reduction of the analyte under static flow conditions. The analyte (4) diffuses on to the sensing electrode (21) through six diffusion openings through the hardware (20) and membrane (6), each opening having a total length-to-diameter ratio of approximately 3 or greater.

Figure 9A:
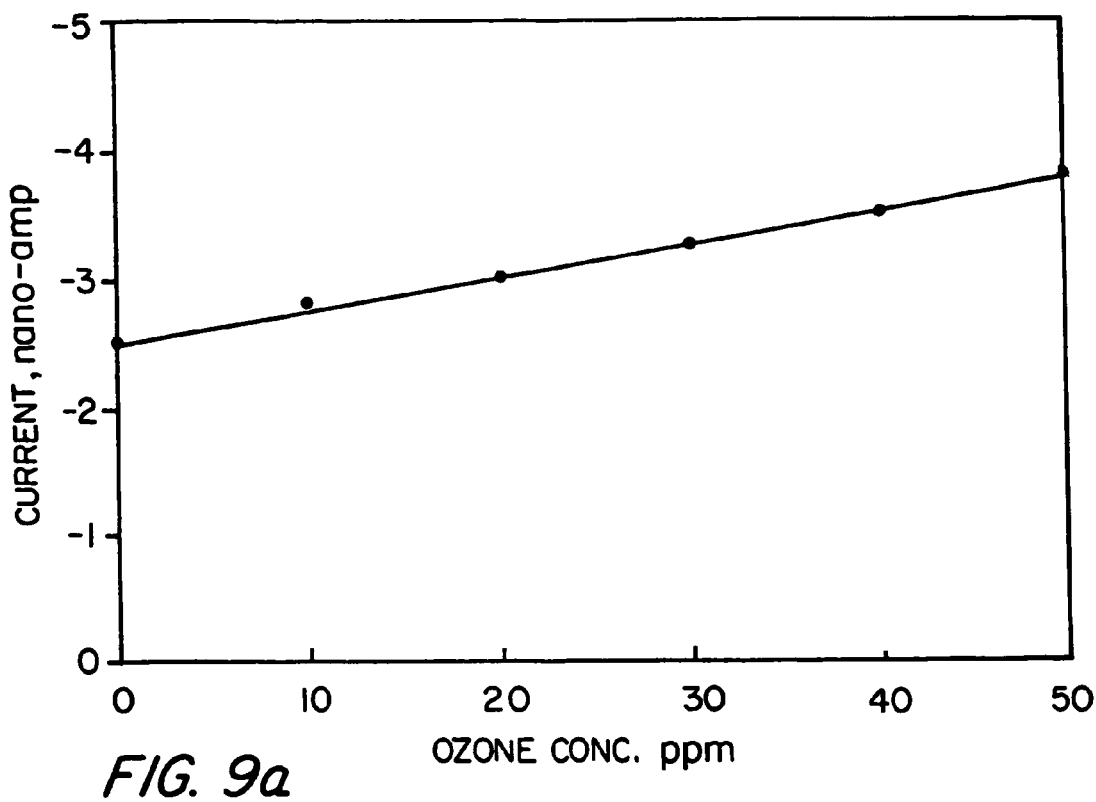
FIGS. 9a and b show calibration curves for ozone in air with flag-type Au sensing electrode.
Figure 9B:
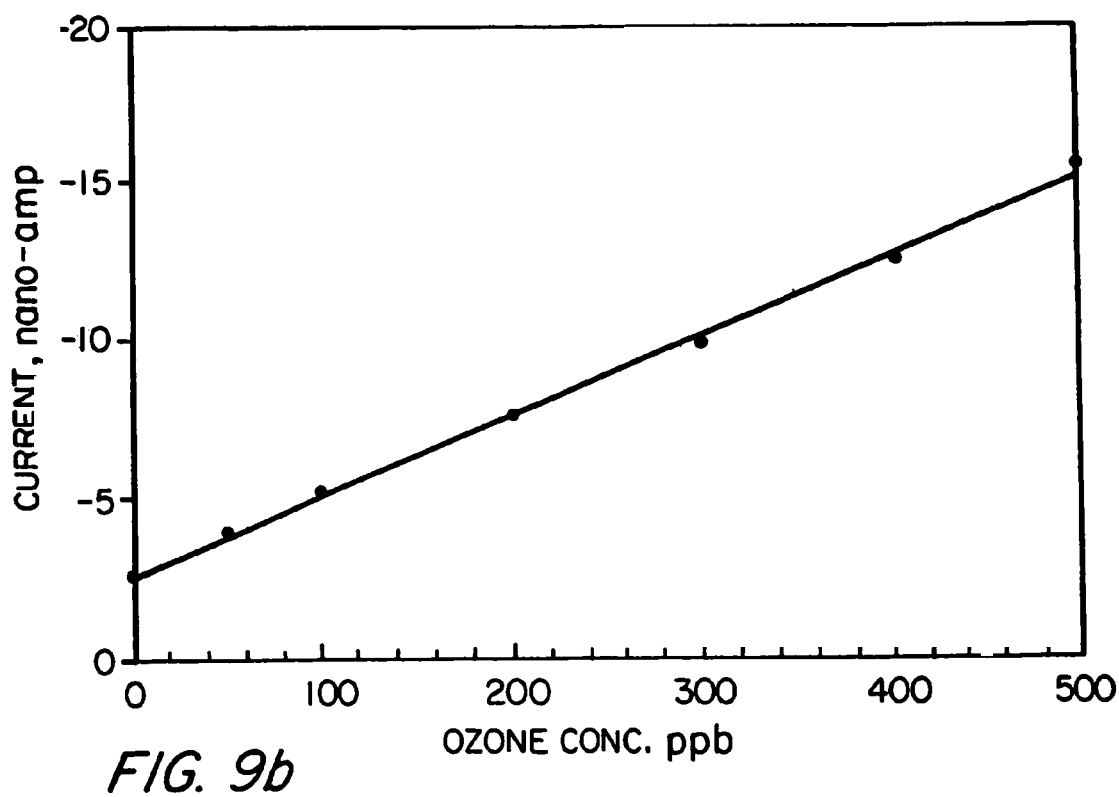
Figure 10:
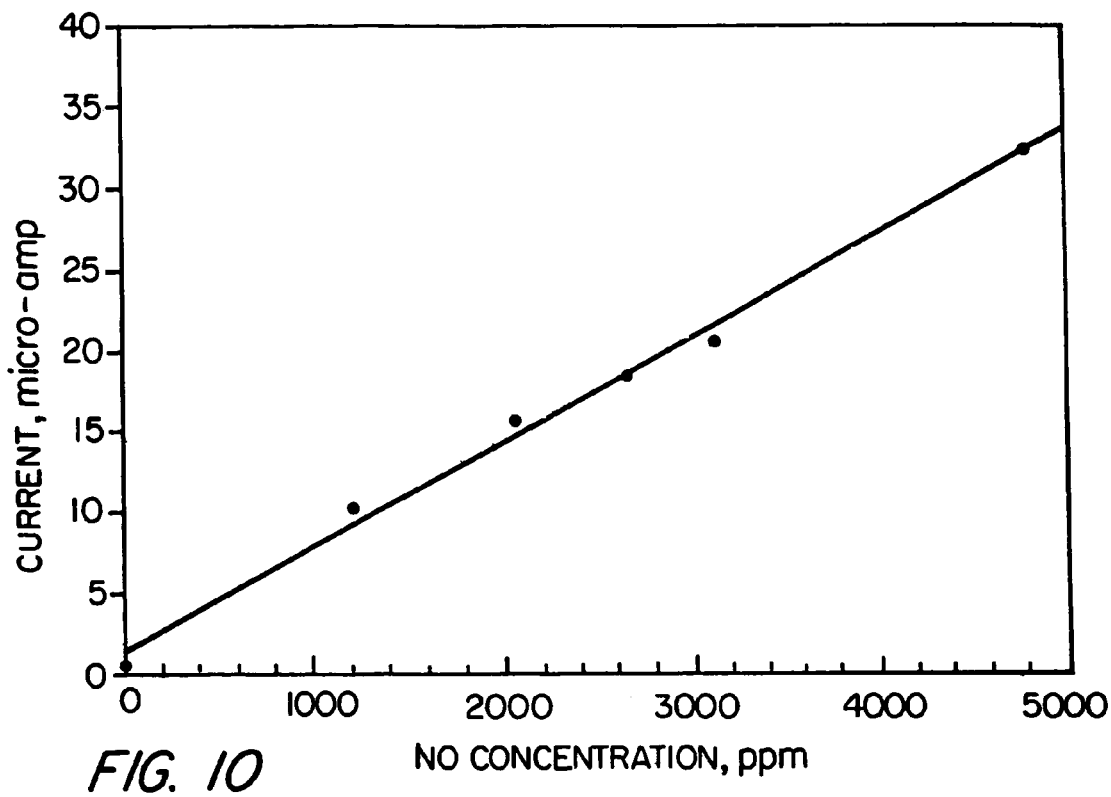
FIG. 10 shows a calibration curve for NO in air with flag-type Au sensing electrode.
Figure 11:
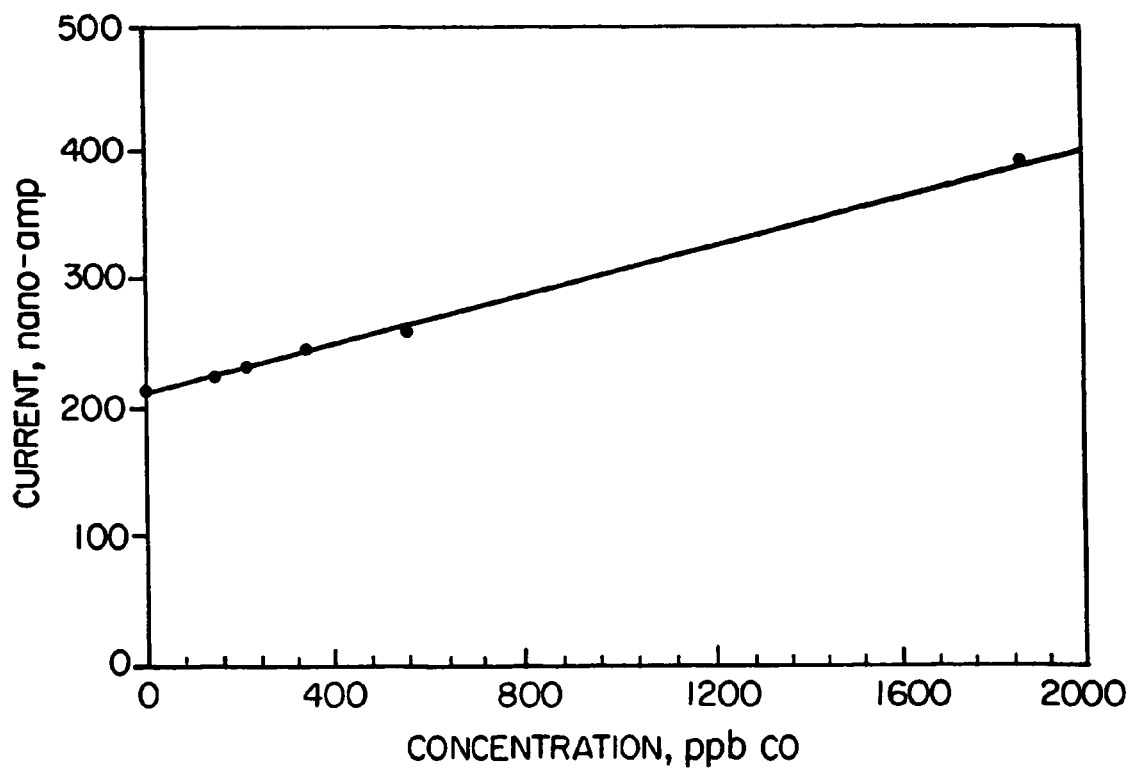
FIG. 11 shows a calibration curve for CO in air with flag-type Pt sensing electrode.

Calibration curves for ozone, NO and CO are shown in FIGS. 9-11 respectively. It should be noted that the measured signal amplitude and low background noise levels obtained with a flag-type sensor (21) design is large enough for the analytes (4) under investigation to be resolved in the single-digit ppb range. A specific advantage of the film type solid polymer ionomer membrane sensor in this invention is the high signal to background noise ratio.

The flag-type film type sensing electrode (21) design can be utilized to measure ethanol, methanol, acetone, hydrazine and hydrogen. Potentiostatic-controlled measurement results for the above mentioned gases are listed in Table-1.

TABLE 1

| Gas/Vapor | Analyte Conc. | Solid Ionomer Electrolyte | SE | Signal |
|---|---|---|---|---|
| Ethanol: | 1 mg/ml | Nafion | Pt | 1.72 micro-amp |
| Methanol: | 2 ml/60 ml | Nafion | Pt | 180 nano-amp |
| Acetone: | 300 micro-l/40 ml | Nafion | Pt | 0.045 micro-amp |
| Hydrazine: | 100 ppb | RAI | Au | 9.3 nano-amp |
| Hydrazine: | 100 ppb | Nafion | Au | 3 nano-amp |
| Hydrogen: | 2.5% | RAI | Au | 120 nano-amp |
| Hydrogen: | 2.5% | Nafion | Au | 150 nano-amp |
| Hydrogen: | 2.5% | RAI | Au | 50 nano-amp |
| Hydrogen: | 2.5% | Nafion | Au | 97 nano-amp |

Figure 2C:
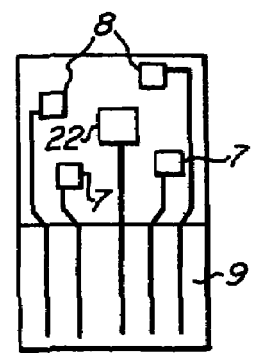
FIG. 2c shows a dot-type film type sensing electrode.

FIG. 2c shows an embodiment utilizing a dot-type film type sensing electrode (22) 2.3 mm in diameter, surrounded by four smaller dots of 1.2 mm dia. each. One of the lower smaller dots is used as a Pt/air reference electrode (7), while the top two smaller dots are used as counter electrodes (8). Counter (8) and reference (7) electrodes are electroplated with Pt black, and when a Pt sensing electrode is desired, it is also electroplated with Pt black. The ionomer membrane (5) is hot pressed onto the film type electrodes. One approximately 1.5 mm dia. opening (6) in the membrane (5) defines the three-phase contact area (2) for the oxidation/reduction of the gas sample (analyte) (4) under investigation. The gas sample (4) stream is conducted over the sensing electrode (22) at moderately low flow rates.

Dot-type film type sensing electrodes (22) are used to measure $NH_3$ and $H_2S$. Potentiostatically controlled measurement results for the above mentioned gases are listed in Table 2.

TABLE 2

| Gas/Vapor | Conc. | Solid Ionomer Electrolyte | SE | Signal |
|---|---|---|---|---|
| $NH_3$: | 114 ppm | Neosepta | Pt | 10 nano-amp |
| $H_2S$: | 14 ppm | Nafion | Pt | 700 nano-amp |

Further embodiments of this invention include utilizing laser ablation methods for creating openings in the ionomer membrane in addition to the traditional methods of die punching. These openings may be of any appropriate shape. A diffusion barrier membrane may be placed over the openings to achieve permeation selectivity. Additionally, a filter material such as Purafil may be placed over, or in, the openings to remove interfering gasses or contaminants. Various heat or bonding methods may be employed for placing the ionomer film or membrane on the film type electrodes or the film type substrates.

The signal response of the three phase contact area can be enhanced through the use of a porous ionomer membrane film over the sensing electrode. Porosity can be achieved by utilizing a casting film of liquid ionomer that contains easily leachable fillers such as starch or polyglycols.

The sensing electrodes can be organized in multiple arrays or sets containing a necessary number of counter or reference electrodes. Reference electrodes such as Pt/air ($O_2$), $PtO_2$, or dynamic hydrogen electrode as described by Giner (1964) may be employed. Electrically driven 3- or 2-electrode film type configurations may be employed using potentiostatic, potentiodynamic or potential control. Two-electrode configurations require a reversible or stable counter-reference electrode such as Pt/air ($O_2$), $PtO_2$ or $Pt/H_2$ which has a higher BET (Brunauer, Emmett, Teller) surface area (25 $m^2/g$ or larger) and/or larger geometric surface areas than the sensing electrode.

Electrochemically reversible electrodes may be used in 3 or 2 electrode configurations, but especially in a 2 electrode arrangement where the counter electrode also acts as a reference electrode. Electrochemically reversible electrodes are constructed of stable catalyst materials and usually have a relatively large electrochemical active surface area so that they remain stable and their potential is not perturbed by small current flow. Examples include $PtO_2$ and Ag/AgCl electrodes.

The sensor may be operated in a potentiodynamic mode of operation which serves to restore the original surface of the sensing electrode after gas or vapor sample adsorbs or perturbs the nature of the surface.

The sensor may also be used to detect other gases or vapors that are easily oxidizable or reducible, such as aldehydes (formaldehyde, acetaldehyde), $Cl_2$, HCl, ethylene, acetylene.

The invention claimed is:

1. A sensor cell, comprising:
    a substrate having a surface for depositing electrodes thereon;
    an electrode in contact with said surface;
    an ionomer membrane in contact with said substrate and having a first location and a second location;
    an opening in said membrane extending from said first location to said second location proximate to said electrode; and
    wherein said opening is generally non-tortuous for defining a passage for a gas to pass freely from said first location to said second location and contact said electrode within said opening.

2. The sensor cell according to claim 1, further including a three-way contact point in said opening between said electrode, said gas, and said ionomer membrane.

3. The sensor cell according to claim 2, wherein said electrode is coated with a thin proton exchange film layer which acts to increase said three-way contact points.

4. The sensor cell according to claim 1, further comprising openings in said membrane proximate to said electrode which facilitate contact in said open three-phase area.

5. The sensor cell according to claim 4, wherein said openings in said membrane contain a particulate catalyst which electrically contacts said sensing electrode.

6. The sensor cell according to claim 1, wherein said electrode is a sensing electrode and further comprising a counter electrode and a reference in contact with said substrate.

7. The sensor cell according to claim 6, wherein said sensing, counter, and reference electrodes are formed by deposition on said membrane.

8. The sensor cell according to claim 6, wherein said sensing, counter, and reference electrodes are formed by deposition on said substrate.

9. The sensor cell apparatus according to claim 6, wherein said sensing, counter, and reference electrodes comprise a material selected from the group consisting of Pt, Au, C, platinized Pt, and platinized Au.

10. The sensor cell according to claim 1, wherein said ionomer membrane is comprised of dispersed metallic particles which act to increase said three-way contact points and to enhance signal response and stability.

11. The sensor cell according to claim 1, wherein said ionomer membrane is humidified by aqueous material.

12. The sensor cell according to claim 1, further comprising a microprocessor for real time data readout, data storage and retrieval, and remote data transmission.

13. The sensor cell according to claim 1 incorporated into a gas sensing instrument.

14. The sensor cell according to claim 1, comprising:
    a plurality of electrode particles dispersed throughout said ionomer membrane;
    wherein said opening defines a passage for a gas to pass from said first location to said second location and contact said electrode within said opening; and
    wherein said plurality of electrode particles increase contact between the gas, electrode particles, and ionomer membrane.

15. The sensor cell according to claim 14, wherein said plurality of electrode particles are selected from the group consisting essentially of platinum, gold, $RuO_2$, metal oxides, and combinations thereof.

16. The sensor cell according to claim 14, wherein said opening provides a concentration gradient from said first location to said second location resulting in a generally steady state flux of gas.

17. A sensor cell, comprising:

a substrate having a surface for depositing electrodes thereon;

an electrode in contact with said surface of said substrate;

an ionomer membrane in contact with said substrate and having a first surface and a second surface;

an opening in said membrane extending from said first surface to said second surface in a location proximate to said electrode for defining a passage;

said opening is generally non-tortuous for defining a passage; and a gas in said opening and simultaneously contacting said electrode and said ionomer membrane for providing a three-way contact between said gas, said electrode, and said ionomer membrane within said opening.

* * * * *